United States Patent [19]

Grabover et al.

[11] Patent Number: 5,785,644
[45] Date of Patent: Jul. 28, 1998

[54] PIVOTAL HANDLE ASSEMBLY FOR A VIDEO OPERATING LAPAROSCOPE

[75] Inventors: Edward Grabover, Brookfield, Conn.; Frank D. D'Amelio, Los Olivos, Calif.

[73] Assignee: Circon Corporation, Santa Barbara, Calif.

[21] Appl. No.: 683,040

[22] Filed: Jul. 12, 1996

[51] Int. Cl.$^6$ ............................ A61B 1/04; A61B 1/22
[52] U.S. Cl. ................................... 600/131; 600/109
[58] Field of Search ........................ 600/131, 109, 600/160, 167, 168, 170, 171, 172, 178, 182, 153, 156, 157, 166, 173, 197

[56] References Cited

U.S. PATENT DOCUMENTS 4,384,570  5/1983  Roberts ........................... 600/196 X

*Primary Examiner*—Beverly M. Flanagan
*Attorney, Agent, or Firm*—Daniel J. Meaney, Jr.

[57] ABSTRACT

A pivotable handle assembly for an endoscope such as an operative laparoscope having a proximal end is shown. The handle assembly includes a handle support operatively connected to the proximal end of a laparoscope. A handle including a mounting end is operatively connected by a member to the handle support. The mounting end is pivotally attached to the handle support enabling the handle to be pivoted relative to the operative laparoscope.

In the preferred embodiment, the operating laparoscope is a video operating laparoscope and includes an image transferring member for producing an optical image at the proximal end of the laparoscope. A video camera is operatively connected to the proximal end to receive the optical image.

A method for using the video operating laparoscope with a pivotable handle assembly in a surgical procedure is also shown.

36 Claims, 5 Drawing Sheets

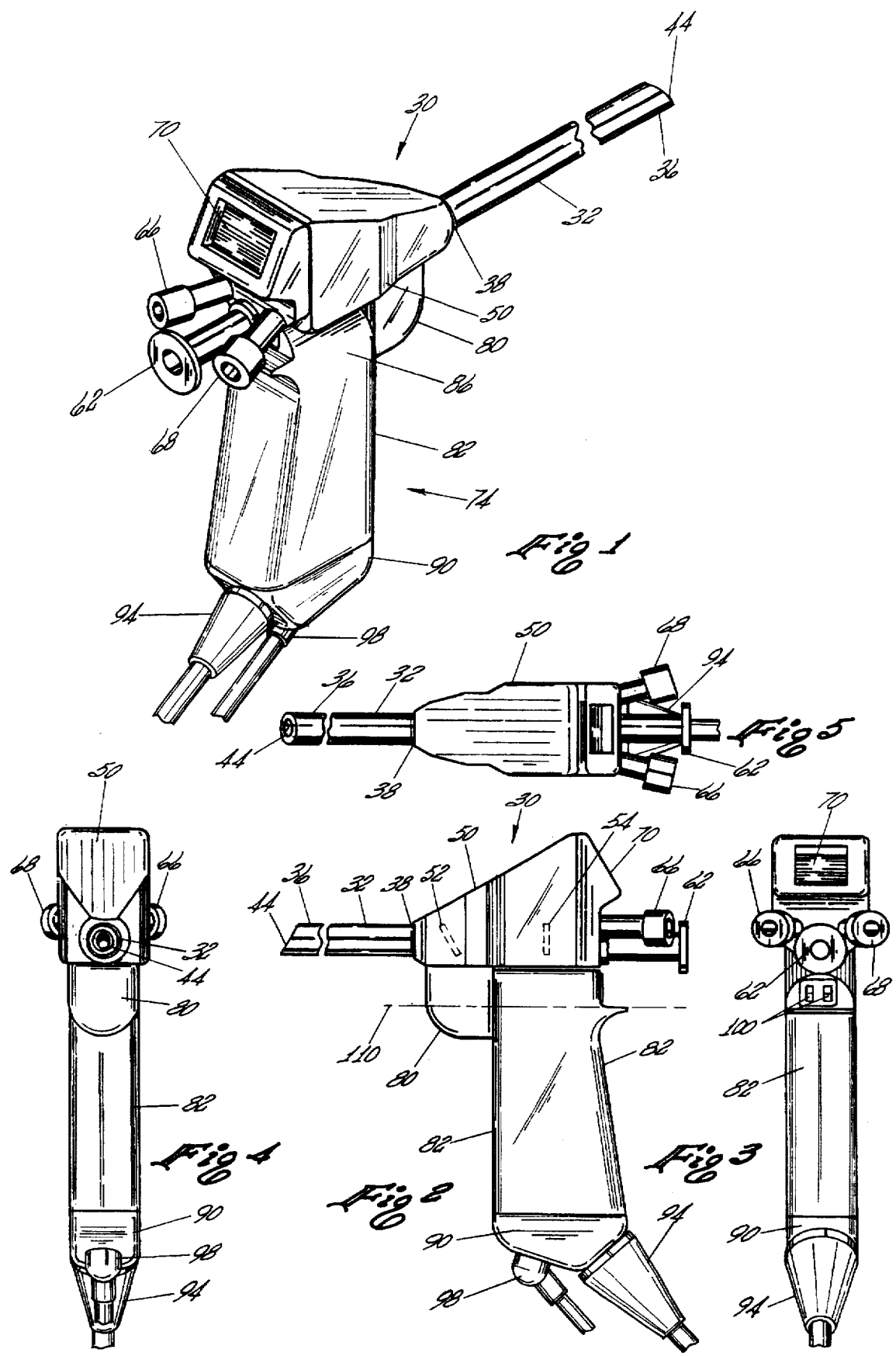

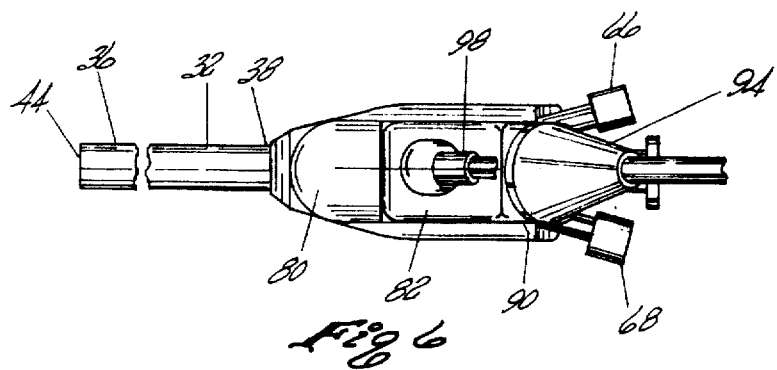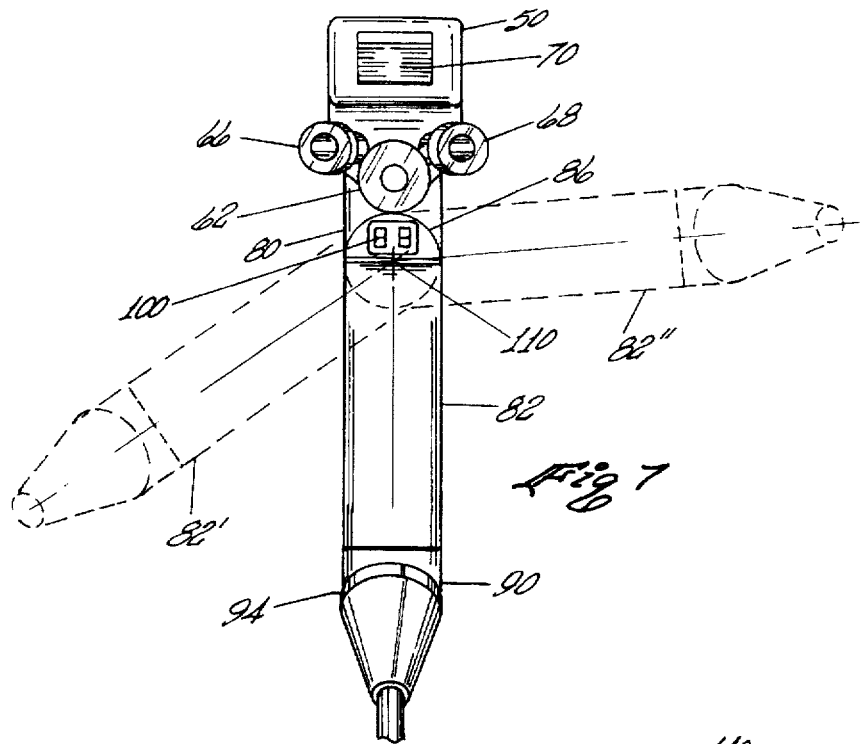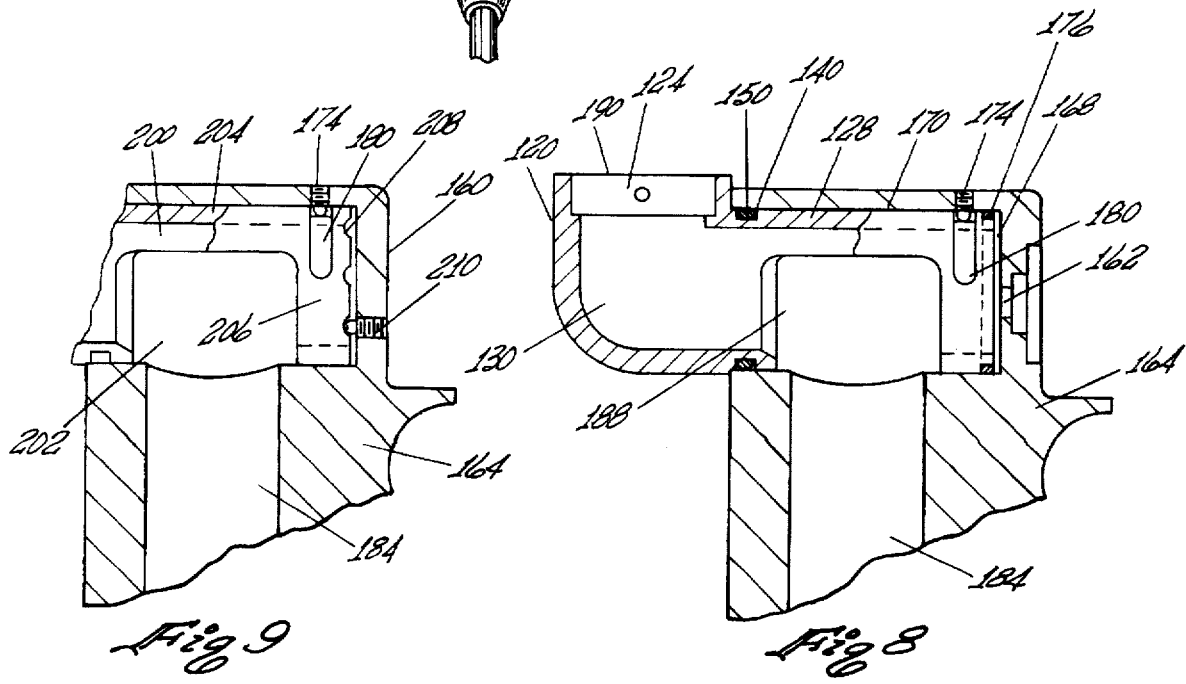

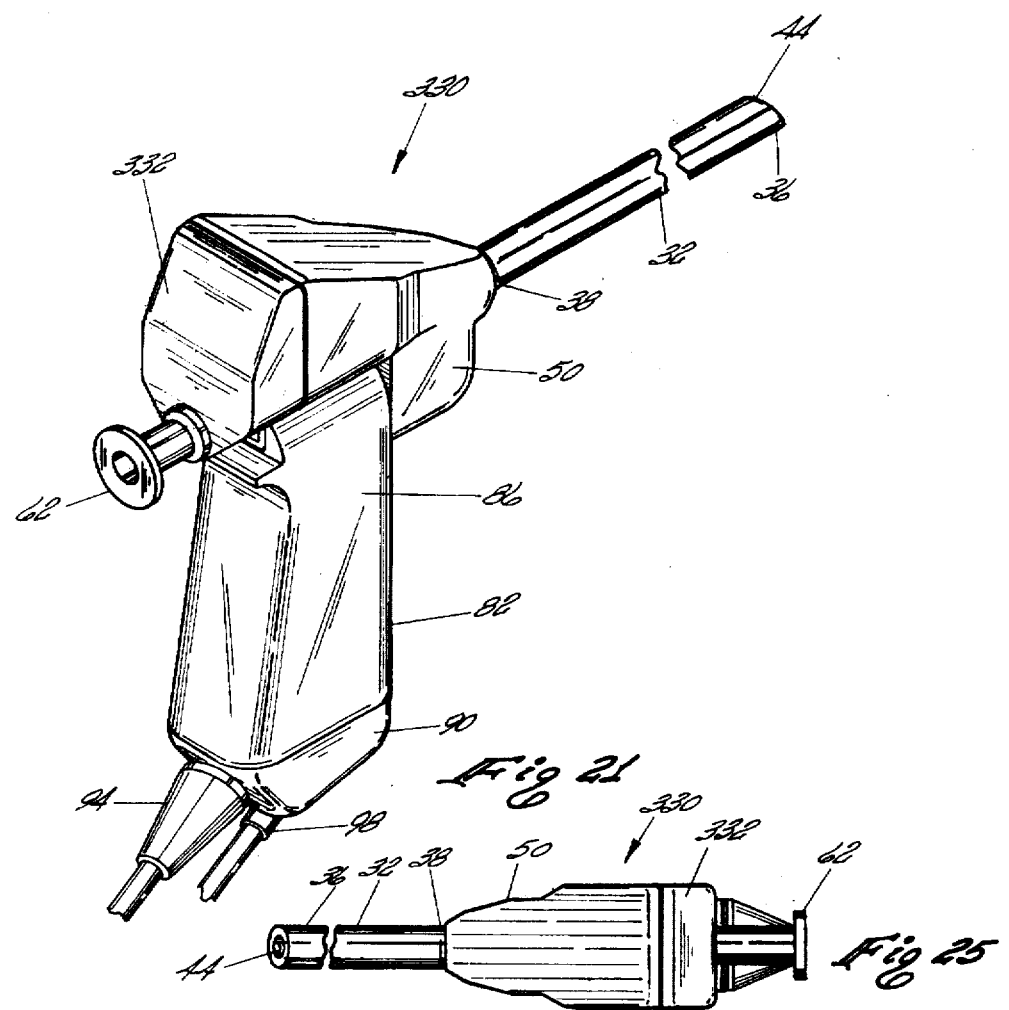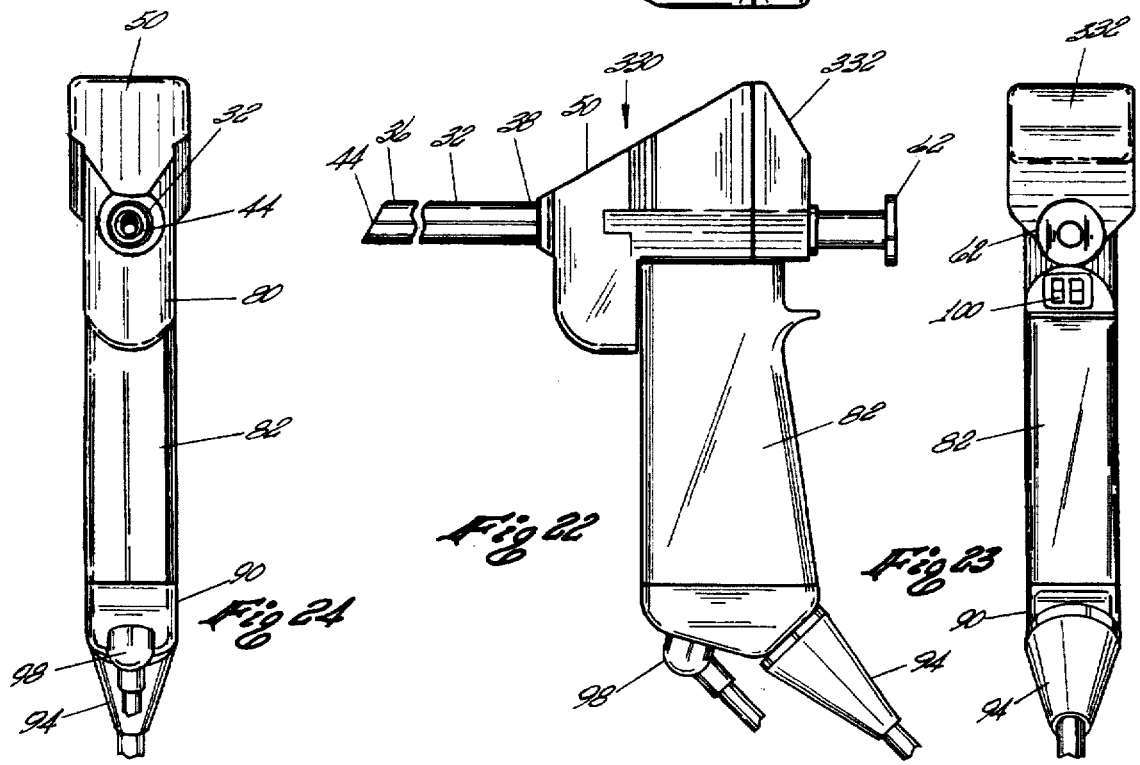

PIVOTAL HANDLE ASSEMBLY FOR A VIDEO OPERATING LAPAROSCOPE

BACKGROUND OF THE INVENTION

1. Field of the Invention

This invention relates to an operating laparoscope which is utilized for performing laparoscopic procedures in a cavity and more particularly is directed to a video operating laparoscope having a handle assembly which includes a pivotal handle which can be pivoted relative to the laparoscope. The video operating laparoscope includes a distal tip having a distal optical lens. In another embodiment, the video operating laparoscope includes a means including a fluid channel for defining a nozzle at the distal tip which is capable of directing a fluid flow across the distal lens to keep the exterior surface free from image impeding material. Additional channels, including an accessory channel and an irrigation channel, can be incorporated in the video operating laparoscope to provide a stream of irrigation fluid for applying suction to a working site or for the passage of working accessories such as laser fibers and electrosurgical probes, including bi-polar probes, ultrasonic probes and the like.

2. Description of the Prior Art

The use of operative laparoscopes for performing laparoscopic procedures is well known in the art. A laparoscope is one class of an endoscope. Endoscopes are used for performing medical surgical procedures. Typically, the state-of-the-art operative laparoscope includes a rigid elongated sheath tube which encloses an image transferring means channel which receives a fiber optic image bundle or relay lens system. The image transferring means channel is typically surrounded by fiber optic light carrying means. The distal end of the laparoscope is used to develop an optical image of an operating site within a cavity, for example, a body cavity, and the operating site is illuminated by light energy which is carried to the operating site by the fiber optic light carrying means. The optical image is transmitted through the image transferring means to the proximal end of the laparoscope where a viewable image is observed by the surgeon. The state-of-the-art laparoscopes are usually inserted through a cannula and trocar assembly which makes an incision or opening in the navel or belly-button of a patient. The purpose of making the incision in the navel or belly-button is to minimize the size of the surgical scar which remains upon completion of the surgical procedure. It is also known in the art to utilize a primary cannula and trocar assembly to form the initial opening through the navel or belly-button into the abdomen or the peritoneal cavity and to use smaller cannula and trocar assemblies which are inserted into other adjacent smaller incisions to provide access to the peritoneal cavity for passing working tools.

In the known laparoscopic procedures, the peritoneal cavity is insufflated with an appropriate fluid such as carbon dioxide ($CO_2$) gas, concomitant with laparoscopic or peritoneoscopic examination, diagnosis and/or treatment, including the excision of structures and tissues in the peritoneal cavity. In the recent past, the type of surgeries and/or procedures performed using laparoscopic instrumentation have been expanded into new minimum invasive surgical procedures.

One such new procedure utilizes the laparoscope, with other appropriate instruments, for performing laparoscopic cholecystectomy which is essentially a minimally invasive surgical method or procedure for removal of a gallbladder. Similar minimally invasive surgical techniques are being developed using laparoscopes to remove other organs, such as the appendix or kidney, or to remove tissue, such as tissue from the liver also located in the peritoneal cavity. Operative laparoscopes are also used in thoracoscopic procedures which are performed in the operative areas of the chest and lungs. Certain of the state-of-the-art operative laparoscopes and video laparoscopes have fixed handles.

In a laparoscopic procedure, the laparoscope having a video camera operatively coupled thereto is utilized to provide the surgeon with a video image of the operating site. The video image is displayed on a color television monitor and that image is used by the surgeon to perform the procedure. To obtain a high quality optical image, a small, highly sensitivity video camera is usually operatively attached to the eyepiece of the laparoscope. In a video operative laparoscope, the eyepiece is eliminated and the video camera is directly or operatively attached to the proximal end of the laparoscope. The surgeon is able to insert and manipulate other instruments through auxiliary cannula and trocar assemblies located at small punctures made in the abdomen, all under the view of the surgeon through the video image developed by the video camera.

Further, it is also known in the art that when utilizing a laparoscope in a laparoscopic procedure, such as, for example, the laparoscopic cholecystectomy described above, it is necessary that the distal lens be free from light or image impeding agents such as a layer of fog, protein material or organic material. It is the desire of the surgeon to keep the laparoscope at the operative site or in the body cavity at all times viewing the original tissue to be treated.

It is known that when the distal tip of the laparoscope is inserted into a body cavity, a fogging occurs across the distal tip which impedes the passage of the optical image and which interferes with the ability of the surgeon to view the operating site. This fogging condition is due to the fact that the operating room temperature is in the order of 20° C. (68° F.). However, the interior of the body cavity or abdomen is generally at blood temperature which is typically in the order of 37° C. (98.6° F.). Thus, when a laparoscope, which is maintained at room temperature in the operating room which is typically 20° C. has the distal tip thereof at room temperature of about 20° C., inserted into the abdomen having a temperature of approximately 37° C., the temperature differential therebetween is sufficient to cause instant fogging of the distal lens.

One known method for solving this problem which is used is to heat the distal tip of the laparoscope by a variety of means. One method that is utilized to heat the distal tip is to insert the distal tip into a container of hot water to raise the temperature of the distal tip to approximately 37° C. Another known technique is to place the distal tip in hot towels to raise the temperature thereof to approximately 37° C.

In addition to the above fogging problem, other image impeding problems are encountered during a procedure. When a surgeon is performing a procedure, that procedure normally results in particulate matter such as protein, blood, tissue and the like being splattered through the operating site during the procedure. Typically, certain of the particulate matter will adhere to the distal surface and transparent member located at the distal tip of the laparoscope and thereby impede the transmission or passage of the optical image through the transparent member. This is particularly true during use of laser and electrocautery procedures for removing tissue.

In a typical laparoscopic procedure, particulate matter accumulates on the distal end three or four times during a procedure. Each time the optical image is impeded by the accumulation of particulate matter, it is necessary for the surgeon to remove the laparoscope from the operative site. If, for example, the operative site is in the abdominal or peritoneal cavity, the laparoscope must be removed from the cannula and trocar assembly, and be physically wiped to remove the particulate matter off of the transparent member located at the distal tip of the laparoscope and then to reinsert the laparoscope through the cannula and trocar assembly back into the abdominal or peritoneal cavity to continue the procedure.

A laparoscope having means for removing image impeding material from a distal lens is described in U.S. Pat. No. 5,207,213 which is owned by the Assignee of the present invention.

Offset operating laparoscopes are also known in the art. Typically, the known offset operating laparoscopes have a rigid elongated sheath with a rigid optical path having two prisms defining an optical channel, a fiber optic light guide and an optical channel. The operating channel port located at the proximal end of the operating laparoscope is coaxial with the optical channel. The rigid optical path extends substantially perpendicular (at about 90°) from the rigid elongated sheath at the proximal end and then through a 90° bend which then extends the rigid optical path along an axis which is parallel to the axis of the rigid elongated shaft terminating in an eyepiece. Prisms are used at each 90° bend of the optical path. The fiber optic light guide enters the rigid elongated sheath at the proximal end and extends from the proximal end to the distal end. The operating channel can be used to pass an electrosurgical instrument such as a monopolar grasping device which can be used to perform surgical procedures such as a tubal ligation. Such offset laparoscopes have been known in the art for more than 15 years.

None of the known prior art devices or procedures disclose, teach or suggest the use of a pivotable handle assembly for an operative laparoscope to enable a surgeon to rotate the pivotable handle in order to maneuver the laparoscope. It is highly desirable to move the laparoscope close to the patient's body in certain procedures. By positioning the laparoscope close to the patient's body, the distal end of the laparoscope can be selectively positioned, as necessary, during the procedure relative to the operative site. The surgeon can pass working instruments through the working channel to perform a procedure including when the laparoscope is positioned very close to the patient's body.

Further, during long surgical procedures, the physician is able to change hands and/or handle position without changing the laparoscope position. This allows the physician to relax her or his hand muscles.

Rotating the handle also allows the physician to offset her or his hand in relationship to the accessory channel. In the known operating laparoscopes, the handle of a 5 mm laparoscopic instrument is fixed resulting in an unrotatable video operation laparoscope. As such, movement of the handle in known video operating laparoscopes which can cause undesirable rotation and/or movement of the laparoscope within the patient.

SUMMARY OF THE PRESENT INVENTION

A novel, new and unique handle assembly for a laparoscope used in operative laparoscopic procedures is disclosed and taught by the present invention. In the preferred embodiment, the laparoscope includes a rigid elongated sheath having a selected length and a proximal end. The handle assembly includes a handle support which is operatively rigidly connected to the proximal end of the laparoscope. The handle assembly further includes a mounting end. The mounting end includes means for operatively moveable, e.g. pivotally attaching, the handle to the handle support to enable the handle to be pivoted relative to the laparoscope.

None of the known state-of-the-art laparoscopes include a handle assembly for enabling the handle to be pivoted relative to the central axis of the laparoscope for allowing the surgeon to concurrently support and maneuver the laparoscope, particularly in the peritoneal cavity or thoracic cavity to be close to the patient's body. Also, the video operating laparoscope can be positioned relative to a patient to facilitate ease of insertion and removal of accessory instruments in the accessory channel.

In addition, another embodiment of the video operative laparoscope having a pivotable handle assembly may include a nozzle for use in overcoming the fogging problem and the accumulation of foreign and particulate matter problem by removing matter that is deposited upon or which adheres to the distal end of the laparoscope thereby impeding or inhibiting the passage of the image through the transparent member.

One advantage of the present invention is that the video operating laparoscope handle assembly includes a handle having a support which is operatively rigidly connected to the proximal end of the laparoscope and a handle having a mounting end. The laparoscope also includes means for pivotally attaching the mounting end of the handle to the handle support to enable the handle to be pivoted relative to the laparoscope. The handle may be in the form of an ergonomic handle grip.

Another advantage of the present invention is that the video operating laparoscope having a pivotal handle assembly includes an image transferring member for producing an optical image at the proximal end of the laparoscope. A video camera or CCD sensor is operatively connected to the proximal end for receiving the optical image.

Another advantage of the present invention is that the video operating laparoscope pivotal handle assembly pivotally attaching means further includes means for fixing the handle at selected pivoted positions relative to the laparoscope.

Another advantage of the present invention is that the distal end optical system has a 6° wedge which allows the physician to view the image of a working instrument distal end or a laser beam dot or spot at a specific working distance in the middle of a video monitor.

Another advantage of the present invention is that the operative laparoscope having a pivotal handle assembly includes a first and second co-acting member for pivotally attaching the mounting end of the handle to a handle support assembly to enable the handle to be pivoted relative to the laparoscope.

Another advantage of the present invention is that the operative laparoscope having a pivotal handle assembly may include an irrigation channel which can be utilized for aiming or directing along a predetermined path a fluid flow, under pressure, across the tissue or organ subject to the procedure to remove organic material matter therefrom while permitting the surgeon to have a clear view during the laparoscopic procedure.

Another advantage of the present invention is that the irrigation channel can be utilized with a high pressure fluid source to perform hydro-dissection of tissue under direct visualization and maneuverability of the operative laparoscope having a pivotal handle assembly.

Another advantage of the present invention is that the operative laparoscope having a pivotal handle assembly can include one or more working channels of various sizes. The working channels can be of the same size or can be of different sizes. The accessory channels or working channel of the laparoscope can be utilized for performing a plurality of procedures including passage of working tools such as an elongated tube or a laser guide through the channel to the operative site, thereby enabling a surgeon to utilize a laser as part of the operative surgery.

Another advantage of the present invention is that the working channel or accessory channel can be utilized with other probes, such as, for example, a coagulation probe or a BICAP® electrosurgical probe.

Another advantage of the present invention is that an accessory channel can be utilized for an irrigation fluid to provide on site irrigation during a surgical procedure.

Another advantage of the present invention is that some of the steps of certain procedures which require "triangulation" can be eliminated by use of the maneuverability of the video operating laparoscope having a pivotal handle assembly. Triangulation is required when one or more instruments are inserted into a cavity through different openings and the distal ends of each instrument are direct at appropriate angles to the operative site. Triangulation is usually required to irrigate an operative site by inserting an irrigation tool through one opening and inserting a laparoscope through a second opening. By using the teachings of the present invention in an operative laparoscope having an irrigation channel and/or working channels, all channels are in substantial parallel alignment with the elongated axis of the rigid elongated sheath and certain procedures can be performed without the triangulation step by rotating the laparoscope relative to the body.

Another advantage of the present invention is that the operative laparoscope having a pivotal handle assembly of the present invention can be in the form of an integrated video operative laparoscope having a CCD chip imaging optics, light guide, working channel and a pivotal handle which can be pivoted over an angle of about 150°. Also, the ergonomic design of the electrical cables and the light cord relative to the handle enables the surgeon to pivot the handle as required without having the pivotal movement restricted by the electrical cable and light cord.

Another advantage of the present invention is that a method for performing surgery utilizing the video operating laparoscope having a pivotal handle assembly of the present invention can include utilizing the operative laparoscope having an accessory channel or working channel which is capable of passing accessories therethrough for performing surgical procedures under direct visualization of the laparoscope. In another embodiment of a video laparoscope having a distal nozzle, any optical image impeding agents, such as protein material, tissue material or the like, which during a surgical procedure becomes deposited upon the distal lens can be removed as follows. The distal nozzle can be activated to direct a fluid flow across the exterior surface of the transparent member to substantially remove the image impeding agent. Thus, the surgeon can perform the entire laparoscopic procedure without removing the instrument from the patient.

Another advantage of the present invention is that a system for performing laparoscopic surgery utilizing an operative laparoscope having a pivoted handle assembly can be used to performing such surgical procedures more efficiently because of the combination of the maneuverability of the operative laparoscope and the ability to pivot the handle relative to laparoscope to move the same close to the patient's body. Further, in an alternative embodiment of a, video operative laparoscope having a pivoted handle assembly and a nozzle located at the distal end the efficiency of performing surgical procedure in the peritoneal cavity a thoracic cavity can be measured by elimination of the requirement that the laparoscope be removed from the peritoneal cavity or thoracic cavity during the procedure.

Another advantage of the present invention is that four control members or buttons are located within fingertip range of the physician on the video operating laparoscope to enable a surgeon, during a procedure, to control with the surgeon's fingertips such functions as distal lens rinse, forward irrigation, video camera gain, accessory control and video printer activation.

BRIEF DESCRIPTION OF THE DRAWINGS

These and other advantages of the invention will be readily apparent when considered in light of the detailed description hereinafter of the preferred embodiment and of the drawings which include the following figures:

FIG. 1 is a top, front and right end perspective view of a video operating laparoscope having a pivotal handle which is the preferred embodiment for practicing this invention;

FIG. 2 is a front elevational plan view of the video operating laparoscope of FIG. 1;

FIG. 3 is a right end elevational view of the video operating laparoscope of FIG. 1;

FIG. 4 is a left end elevational view of the video operating laparoscope of FIG. 1;

FIG. 5 is a top plan view of the video operating laparoscope of FIG. 1;

FIG. 6 is a bottom plan view of the video operating laparoscope of FIG. 1;

FIG. 7 is a right end elevational view of a video operating laparoscope showing various selected positions of the pivotal handle relative to the central axis of the laparoscope;

FIG. 8 is a partial cross-sectional front elevational view of the handle assembly showing one embodiment of a means for pivotally mounting a handle on the handle support;

FIG. 9 is a partial cross-sectional front elevational view of a handle assembly similar to FIG. 8 further including a means located in the handle support and monitor end of the handle for locking the pivotally mounting a handle at selected pivoted positions;

FIG. 21 is a top view, front and right side perspective view of another embodiment of a video operating laparoscope with a pivotal handle assembly of the present invention;

FIG. 22 is a front elevational plan view of the embodiment shown in FIG. 21;

FIG. 23 is a right side elevational view of the embodiment shown in FIG. 21;

FIG. 24 is a left side elevational view of the embodiment shown in FIG. 21; and

FIG. 25 is a top plan view of the embodiment shown in FIG. 21.

DESCRIPTION OF THE PREFERRED EMBODIMENT

Figure 10:
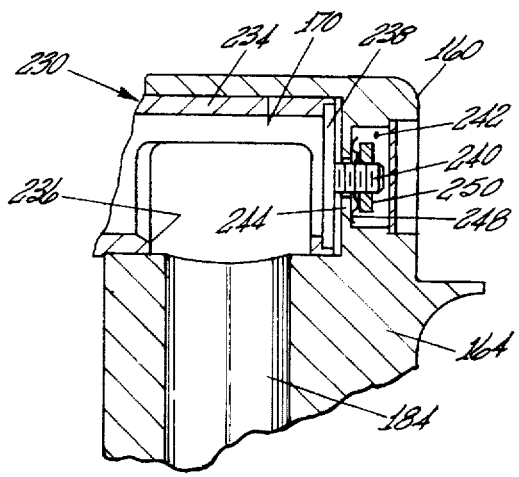
FIG. 10 is a partial cross-sectional front view showing another embodiment of a means for pivotally mounting a handle on a handle support.

FIG. 1 illustrates a laparoscope, shown generally as 30, which is an operative laparoscope having a pivotal handle assembly. In the preferred embodiment, the laparoscope 30 is a video operating laparoscope. FIGS. 2 through 6 likewise show the structural details of the preferred embodiment and the references therein are the same as the references used in connection with the description of FIG. 1. The laparoscope 30 includes a rigid elongated sheath tube 32 having a selected length, a distal section or distal end 36 and a proximal section or proximal end 38. The distal end 36 terminates in a distal tip 44, which preferably is wedge-shaped, for example 6° the proximal end 38 terminates in a housing member shown generally as 50. The housing member 50 encloses an image transferring member or means for transferring an image from the distal tip 44 through the rigid elongated sheath tube 32 to the proximal end 38 of the laparoscope. The housing member 50 also encloses a light guide and operating or working channels which extend through the rigid elongated sheath tube 32 TUV proximal end to the distal end 44. The housing member 50 encloses a video sensor or video camera, shown as dashed sensor element 54 in FIG. 2. Sensor element 54 is operatively coupled to the image transferring member. A $CO_2$ laser adapter 62 communicates with an accessory or working channel which extends from the housing member 50 through the rigid elongated sheath 32 from 38 to the distal end 44. Entry ports 66 and 68 communicate with a lens rinse channel and irrigation channel which, likewise, extend through the housing member 50 and through the rigid elongated sheath 32 to the distal end 44. The lens rinse channel is operatively coupled to entry port 66 and is used to apply fluid to a nozzle for cleaning impeding agents or material off of the distal lens. The video sensor 52 is located within the housing member 50 and receives an optical image from the image transferring means and converts the optical image into a video signal which is ultimately processed by a video processing means to produce a video image in a monitor or as video signals, which may be in the form of digital video signals, for storage of the video image on magnetic media or other storage means.

A beam splitter shown by dashed element 52 in FIG. 2 may be used, in a manner which is known to those skilled in the art, for directing a portion of an optical image along a first path and the remaining position of the optical image during a second path. An eye piece located in housing member 50 and a video sensor 52, which may be a CCD sensor or a video camera, are positioned one each above the first path or second path to recover the optical image.

The housing member 50 also encloses an electrical conductor and a light guide. The electrical conductors are operatively connected to the video sensor or video camera for passing video signals. The light guide extends through the rigid sheath 32 to the distal end 44 to illuminate the operative site.

The video operating laparoscope of FIG. 1 includes a pivotal handle assembly for a laparoscope which is shown generally as 74. The handle assembly 74 includes a handle support 80 which is fixedly operatively connected to the proximal end 38 of the laparoscope 30. A handle 82 having a mounting end 86 which cooperates with means for pivotally attaching the mounting end 86 of handle 82 to the handle support 80.

The handle 82 can be pivoted about the handle support 80 by pivoting the mounting end 86 relative to the handle support 80. In the preferred embodiment, the handle 82 can be rotated approximately 150°.

The handle 82 has a bottom end 90 which is adapted to receive and support an electrical cable 94, which encloses electrical conductors for the video sensor. The electrical conductor extends through the central area of handle 82 to the housing member 50. In addition, the bottom end 90 receives and supports a light guide 98 which extends through the central area of the handle 82 to the handle support 80 and then to the housing member 50. The light guide then extends from the housing member 50 through the rigid elongated sheath 32 to the distal end 44.

The housing member 50 has a well 70 positioned to be viewed by the surgeon. Well 70 may be used to produce and/or display an optical image or an electronically displayed image, such as for example a video image, or convey data to the surgeon.

The handle support 80 may include electrical control members such as, for example, fingertip response control buttons 100 to enable a surgeon to easily control ancillary devices during a surgical procedure. Control buttons shown as 100 are operatively connected to the electrical conductor and are used to electrically control necessary functions such as, for example, to perform control functions, such as video boost, to actuate a video image recording or storage device, to activate lens rinse, to activate forward irrigation, change video camera gain and to contrast accessory devices, e.g. a video printer video sensor.

FIGS. 2, 3, 4, 5 and 6 show the relationship and positions of the various elements in the video operative laparoscope. FIG. 2 illustrates that the axis of the handle support 80 and the mounting end 80 of handle 82 are coaxially aligned as shown by dashed line 110. The axis 110 is essentially spaced from and substantially parallel to the central axis of the rigid elongated sheath 32.

FIG. 7 illustrates the various selected pivoted positions into which the handle 82 can be pivoted. The handle support 80 has the axis 110 extending therethrough. The handle support 80 is operatively pivotally coupled to the mounting end 86 of the handle 82 by an appropriate coupling member or means for pivotally attaching the handle 82 to the handle support 86.

The handle 82 is pivoted at its mounting end 86 around the axis 110 into a desired angular position. For example, phantom handle 82' shows a first selected pivoted handle positioned on one side of the rigid elongated sheath 32. Phantom handle 82' shows a second selected pivoted handle positioned on the other side of the rigid elongated sheath 32.

The surgeon can pivot or rotate the handle 82 to maneuver the operative laparoscope as necessary relative to a patent body while concurrently providing a rigid member for holding onto the video operative laparoscope.

FIG. 8 illustrates a partial assembly view of a handle support 120 which comprises one embodiment of a handle assembly for practicing this invention. The handle support 120 is in the form of an "L" shaped, elongated thin walled tubular member having a connecting end 124, a support shaft 128 and a hollowed out central area 130. The connecting end 124 is operatively coupled to the proximal end of a laparoscope to form a rigid support for the handle assembly. The support shaft 128 functions as a central hub having an outer surface with a bearing member and has a circumferential groove or slot 140 located near the connecting end 124. The circumferential groove or slot 140 is adapted to cooperate with a resilient engaging member such as an "O" ring element 150 which is located in the mounting end 160 of the handle 164 as described herein.

The handle 164 includes the mounting end 160 which defines a hollowed out central area defining a hub receiving opening 168 which has an inner wall 170. Inner wall 170 is adapted to slidably or rotatably cooperate with the hub 128 such that the handle 164 can be pivoted about the hub 128 and bearing number 176.

A locking member 174 cooperates with a detent slot 180 to enable the handle 164 to be rotated to selected pivotal positions.

The interior of the handle 164 defines a passageway 184 which communicates with an elongated opening 188 within the handle support 120. The elongated opening 188 communicates with the hollowed out central area 130. The connecting end 124 has an aperture 190 which communicates with the housing member 50. The passageway 184, elongated opening 188, hollowed out central area 130 and aperture 190 are dimensioned to pass the electrical cables from the cable 94 and the light guide 98 (both illustrated in FIG. 1).

FIG. 9 shows another embodiment of a handle support 200. The handle support 200 includes an elongated opening 202 and a support shaft 204 which functions in the same manner as elongated slot 188 and support shaft 128 of FIG. 8. The handle 164 has the passageway 184 which cooperates with the elongated opening 202 to pass the electrical conductor and light guide as described in connection with FIG. 8. The handle support shaft 204 has an end plate 206 which is a plurality of locking slots 208.

The mounting end 160 of the handle 164 has a resilient locking member such as a spring locking member 210 which cooperates with one of the locking slots 208 to enable the surgeon to lock the handle at selected pivoted positions.

FIG. 10 illustrates an alternate embodiment of a handle support 230 having a support shaft 234 which is a hub for receiving the hub receiving opening defined by inner wall 170. The handle support 230 includes an elongated opening 236 which cooperates with the passageway 184 in the handle 164.

The handle support 230 has an end plate 238 which has a connecting member such as threaded member 240 rigidly mounted thereon. The mounting end 160 of handle 184 has a mounting opening 242 which terminates in a mounting plate 244 having an aperture formed therein to permit the mounting end 160 to be operatively mounted on the threaded 240. A spring loaded spacer washer 248 and a cooperating threaded connecting member 250 is then affixed, placing the spring loaded washer 248 under tension to pivotally support the handle 164 to the handle support 230. The tension of the spring loaded washer 248 is maintained at a level to permit pivoting a rotation of the handle 164 relative to the handle support 230.

Figure 11:
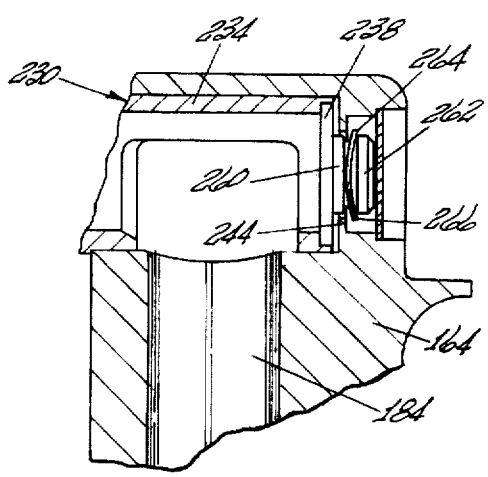
FIG. 11 is a partial cross-sectional front view of yet another embodiment of a means for pivotally mounting a handle on a handle support.

FIG. 11 illustrates another embodiment of a means for pivotally attaching a handle 184 to the handle support 230. In FIG. 11, the end plate 238 has rigidly mounted thereon an extended boss 262 having a slot 264. The slot 264 is adapted to receive a snap ring 266 which forms a clamping force between the mounting plate 244 and the walls of the slot 264. The clamping force is at a level to permit the handle 164 to be rotated around the extended base 262.

Figure 12:
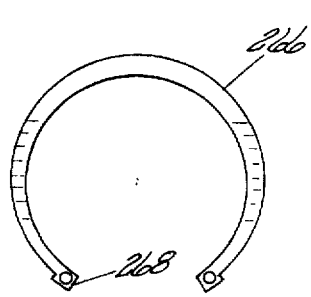
FIG. 12 is a front elevational view of a snap ring for attaching the handle mounting end to the handle support illustrated in FIG. 11.

FIG. 12 shows the snap ring 266 in greater detail and the snap ring 266 has ends 268 to spread the snap ring 266 to load the same into the slot 264 as shown In FIG. 11.

Figure 13:
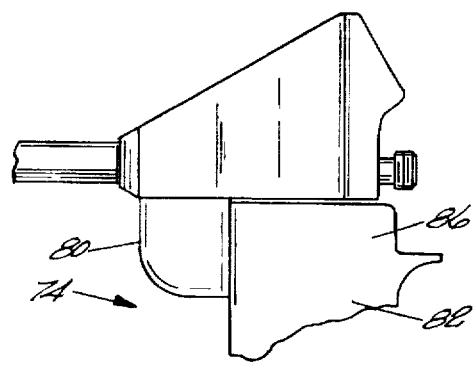
FIG. 13 is a partial cross-sectional front elevational view of a pistol grip shaped handle pivotally mounted to a handle support.

FIG. 13 illustrates the preferred embodiment of the pivotal handle assembly 74 utilizing the structure shown In FIG. 8 having the handle support 80 and handle 82 having the mounting end 86.

Figure 15:
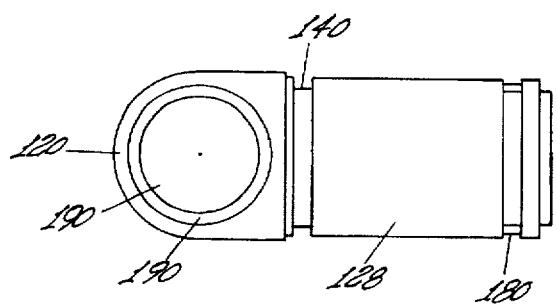
FIG. 15 is a top plan view of a sub-assembly formed of the handle support of FIG. 14.
Figure 16:
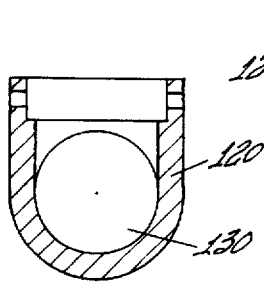
FIG. 16 is a left end elevational view of the handle support of FIG. 14.
Figure 14:
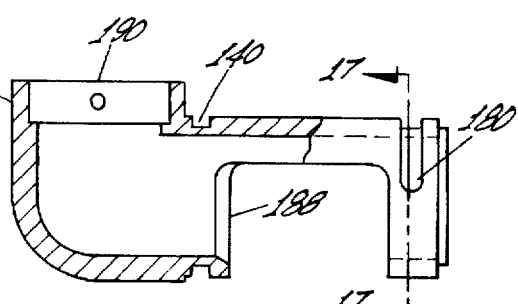
FIG. 14 is a cross-sectional front plan elevational view of a handle support which is adapted to be operatively, rigidly connected to the proximal end of a laparoscope.

FIGS. 14, 15, 16 and 17 illustrate in greater detail the structure of the preferred handle support 120. FIGS. 14 and 15 show the circumferential slot 140 and the circumferential detent groove 180. FIG. 16 shows that the hollowed out central area 130 has a dimension to accommodate the electrical cables and light guide.

Figure 17:
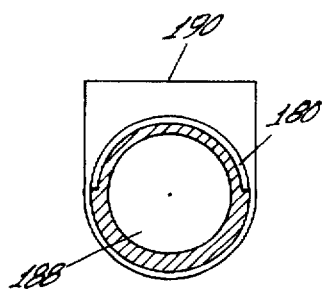
FIG. 17 is a right end elevational view of the handle support of FIG. 14.

The sectional view FIG. 17 taken along section lines 17—17 of FIG. 14 shows the depth of the circumferential detent groove 180.

Figure 18:
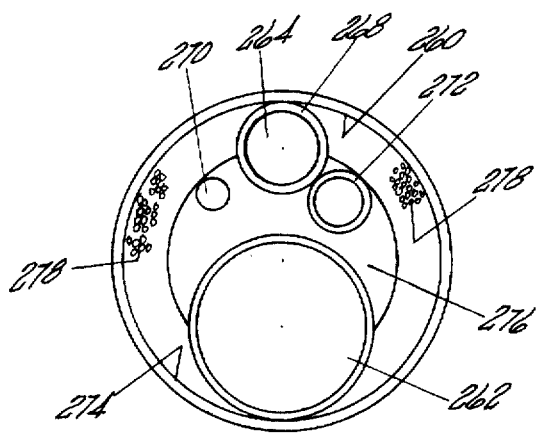
FIG. 18 is a pictorial representation of the distal end of an embodiment of an operating laparoscope showing relationship between an the image transferring means, a channel adapted to be connected to a nozzle, an irrigation channel and accessory channel and a fiberoptic light guide.

FIG. 18 depicts pictorially a cross-sectional end plan view of the distal section of the rigid sheath 32 near the distal tip 94. The rigid sheath 32 is thin walled and defines a central cavity shown generally as 260. The central cavity 260 encloses an optical image transferring member 264 located in an image transferring member channel 268. The image transferring member can be fabricated from any known optical system such as, for example, a lens relay system, a fiber optic image bundle or a GRIN lens system.

A working channel 262 extends substantially co-axially with the optical image transferring channel 264.

Also, a lens irrigation channel 272 is located in a supporting insert 276 located within central cavity 260. In the alternative, the laparoscope may include a lens rinse channel 270 to supply fluid to a nozzle 280 as described relative to FIG. 19. The irrigation channel 272 or the working channel 60, and lens rinse channel 270 are located in the supporting insert 276 and within the central cavity 260.

For purpose of example, irrigation channel 270 could cooperate with entry port 66 shown in FIG. 1, accessory channel 268 could communicate with entry port 68 shown in FIG. 1 and accessory channel 220 could communicate with $CO_2$ adapter 62 shown in FIG. 1.

In FIG. 18, the opening or space remaining between the inner wall 274 of the rigid sheath 32 and the image transferring member channel 268, the supporting insert 276 and the accessory channel 262 is filled with a light guide, such as, for example, a fiber optic light guide bundle depicted by 278.

The geometry and relative size of the channels illustrated in FIG. 18 are examples only and the diameter of each channel, the number of working channels, the use of a nozzle or the like can be varied as required.

Figure 19:
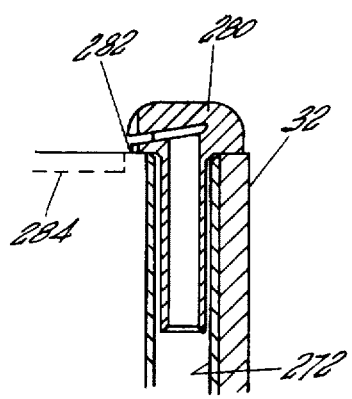
FIG. 19 is a partial cross-sectional side view showing the preferred embodiment of a structure of a nozzle for producing a shaped fluid discharge from the nozzle.

FIG. 19 illustrates pictorially a nozzle 280 for performing the function of using an irrigation fluid to remove image impeding materials from the distal end 282 of the laparoscope. The distal end 282 includes a transparent member or optical image member shown by dash box 284. The transparent member depicted by dashed box 284 may be a distal lens or a CCD chip located at the distal tip 282.

Figure 20:
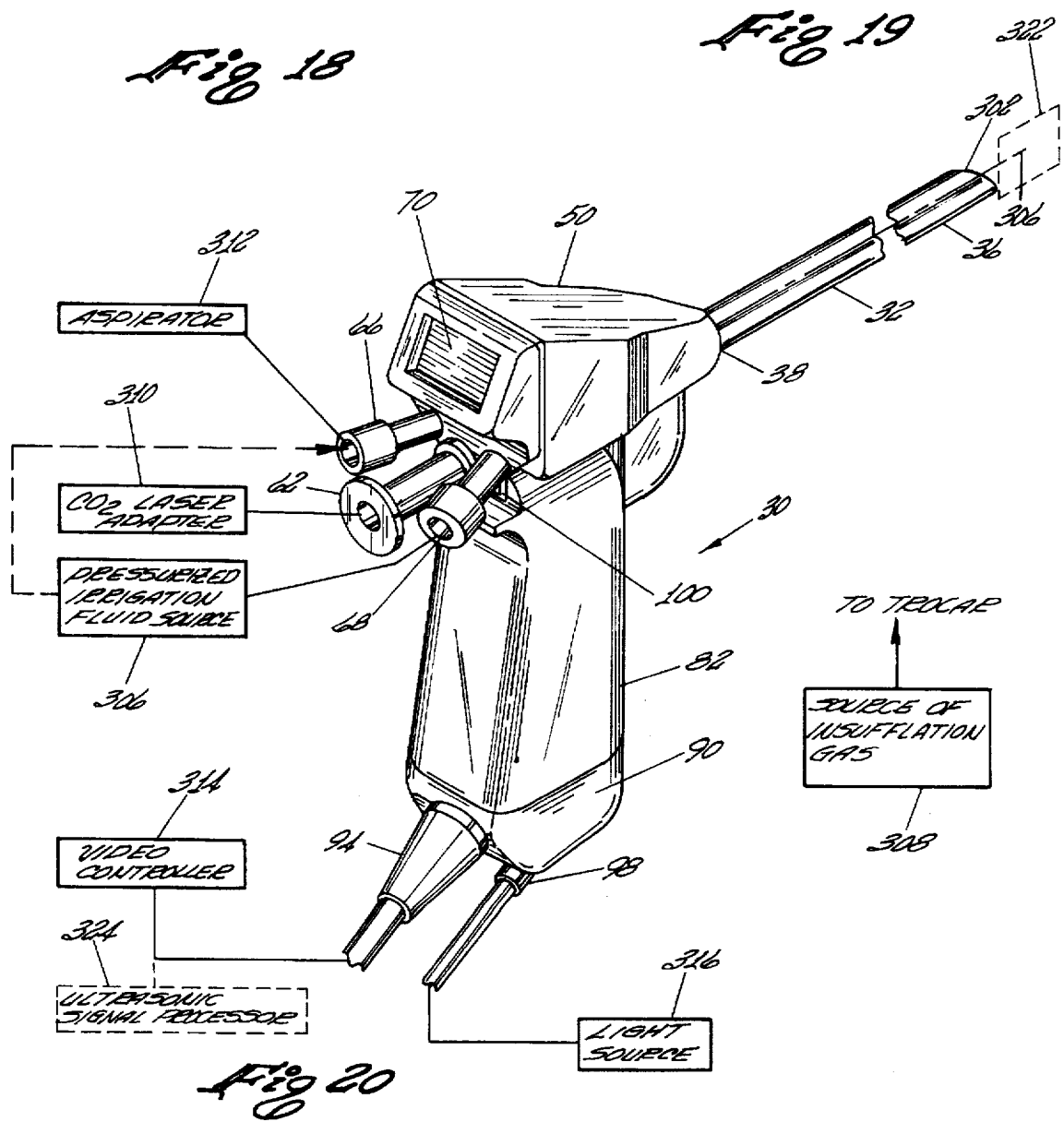
FIG. 20 is a top front and right end perspective view of a video operating laparoscope as part of a system for performing laparoscopic procedures.

FIG. 20 illustrates pictorially a system for performing laparoscopic procedures. In the preferred embodiment, the system includes a video operating laparoscope 30 comprising a rigid elongated sheath tube 32 having an elongated axis 300. The distal section 36 has a proximal section which terminates in a proximal end 38. The distal section 36 has a means for defining a distal tip 44 including fluid tight distal lens 302. The distal lens 302 has an exterior surface located at the distal tip 44.

The rigid elongated sheath 32 encloses means for defining an image transferring means, shown as element 262 in FIG. 18, which extends from the distal tip 44 to the proximal end 38 of the rigid elongated sheath tube 32. The rigid elongated sheath tube 32 also encloses a means for defining a fiber optic light guide, shown as element 278 in FIG. 18, means which extends from the distal tip 44 to the proximal end 38 of the rigid elongated sheath tube 32.

The rigid elongated sheath tube 32 also encloses a means located within said rigid elongated sheath tube for defining at said distal tip 44 a nozzle 280 (FIG. 19) for directing a fluid flow across the exterior surface of said distal lens 302 to remove therefrom optical image impeding agents. Similarly, a means defining a first channel, such as channel 272 in FIG. 18, which extends axially from the proximal end 38 of the rigid elongated sheath tube 36 to the distal tip 44. The first channel is operatively coupled to the means defining the nozzle 280. The first channel 286 including means for defining the proximal end an opening or port 68 which is adapted to be operatively connected to a source of pressurized fluid 306.

The rigid elongated sheath 32 includes means for defining a irrigation channel, shown as 270 in FIG. 18, which extends axially from the proximal end 38 of the rigid elongated sheath tube 32 to the distal tip 44. The second channel 270 includes a means for defining an orifice for directing a stream of fluid along a path which is substantially in alignment with the direction of view of the image transferring means 264. The proximal end of the irrigation channel 270 is operatively coupled to entry port 66.

The system having the video operative laparoscope 30 further includes a $CO_2$ laser adapter 310 which cooperates with the port 62, of course, if necessary for a procedure, the system may includes means defining a source of insufflation gas 308, which includes means for regulating the flow rate and pressure of the insufflation gas which is typically operatively connected to means for passing the insufflation gas such as an insufflation needle in a trocar. A means including a video camera located within the housing member 50 and video signal processing means such as a video controller 314 is operatively coupled to cables 94 which is located at the bottom 90 of the handle 82. The video controller 314 processes video images of the laparoscopy procedures.

The system includes a light source 316 operatively connected to the fiber optic light guide means 98 at the bottom 90 of the handle 82.

In operation, the means including a source of fluid under pressure 306, which is operatively connected to either the entry port 68 or entry port 66, selectively apply fluid under pressure to at least one of the lens rinse channel 272 to direct a fluid flow across the exterior surface of the transparent member and the irrigation channel 270 to produce an irrigating fluid along a path substantially parallel to the direction of view of the video operative laparoscope 30. Alternatively, an aspiration 312 could be used with a port, e.g. port 66.

Although the preferred embodiment herein is in the form of a pivoted handle assembly for a video operative laparoscope, the teaching hereof can apply a laparoscope without any operating accessory or working channels which is typically used is endoscopy procedures.

The preferred embodiment of the video operative laparoscope utilizes an image transferring means, e.g. an optical transferring member. In the alternative, the distal end 36 of the elongated shaft 32 could be adapted to use a deflectable distal tip having a sensor, such as in example, an ultrasonic transducer in a CCD sensor, and the sensor is depicted by dashed box 332. In such an endoscope the option of channel would be used to enclose an electrical conductor. The ultrasonic transducer would be operatively electrically connected in electrical conductor 94 to an ultrasonic signal processor depicted by dashed box 324.

FIGS. 21 through 25 illustrate another embodiment of a video operating laparoscope 330 with a pivotal handle assembly of the present invention. FIG. 21 shows that the video operating laparoscope 330 is a simplified version and includes only some of the elements illustrated in FIGS. 2 through 7. In the video operating laparoscope 330, the entry port 62 is operatively connected to the working channel 262 illustrated in FIG. 8. In addition, the well 70 is eliminated and replaced by a smooth surface 332, as illustrated in FIG. 23 the video operating laparoscope includes fingertip control button 100.

The teaching hereof can be used with an operative laparoscope having a sensor located directly on the distal tip. Also, the teaching of this invention can apply to an operative laparoscope having an eyepiece wherein the operative laparoscope would have at least one operating accessory or working channel for passing work tools, instruments or other enable a surgeon to perform an endoscopic procedure. The sheath of the laparoscope can be either rigid or flexible.

In industrial applications, the pivoted handle assembly of the present invention can be used with a boroscope having a rigid elongated sheath to enable the user to maneuver the proximal end thereof during use of the boroscope in performing a task, such as, for example, inspecting the interior of a cavity, such as for example, the inside of a jet engine.

The pivotal handle assembly of the present invention provides the user with the ability to maneuver the distal end of an instrument within an operative site for viewing, diagnostic and therapeutic purposes.

What is claimed is:

1. A pivotal handle assembly for an endoscope having a proximal end comprising:

a handle support having an opening extending therethrough for enclosing a light carrier and electrical conductors, said handle support being operatively connected to the proximal end of an endoscope;

a handle having an opening extending therethrough for enclosing a light carrier and electrical conductors, said handle support being including a mounting end; and means operatively coupled to said handle support and said mounting end for pivotally attaching said handle to said handle support and for passing therethrough said light carrier and electrical conductors wherein said light carrier and said electrical conductors are enclosed by said handle support, said handle and said pivoting means.

2. A pivotal handle assembly for an endoscope having a proximal end comprising:
a handle support operatively connected to the proximal end of an endoscope;
a handle including a mounting end; and
means operatively coupled to said handle support and said mounting end for pivotally attaching said handle to said handle support, said pivoting means includes a hub located on the handle support and a hub receiving opening located on the mounting end for cooperating with said hub to enable said handle to pivot about said hub.

3. The pivotal handle assembly of claim 2 wherein said pivoting means includes a plurality of locking detents located on the mounting end and a locking member located on the handle which cooperates with said locking detents to lock said handle at a selected pivotal position.

4. The pivotal handle assembly of claim 2 wherein said hub is defined by a cylindrically shaped thin walled, elongated surface which cooperates with an inner wall defined in the hub receiving opening located on said mounting end.

5. A handle assembly for a laparoscope having a proximal end comprising:
a handle support having an opening extending therethrough for enclosing a light carrier and electrical conductors, said handle support being operatively connected to the proximal end of a laparoscope;
a handle having an opening extending therethrough for enclosing a light carrier and electrical conductors, said handle support being including a mounting end, and
means operatively connected to said handle support and said mounting end for pivotally attaching said handle to said handle support to enable the handle to be pivoted relative to the laparoscope and for passing therethrough said light carrier and electrical conductors wherein said light carrier and electrical conductors are enclosed by said handle support, said handle and said pivoting means.

6. The handle assembly of claim 5 wherein said pivotally attaching means further includes means for locking said handle at a selected pivotal position relative to said laparoscope.

7. The handle assembly of claim 5 wherein said pivotally attaching means includes a first co-acting member and second co-acting connecting member for pivotally attaching said mounting end of said handle to said handle support while enabling said handle to be pivoted about said handle support.

8. A handle assembly for a laparoscope having a proximal end comprising:
a handle support having an opening extending therethrough for enclosing a light carrier and electrical conductors, said handle support being operatively connected to the proximal end of a laparoscope;
a handle having an opening extending therethrough for enclosing a light carrier and electrical conductors, said handle support being including a mounting end; and
a first co-acting member and second co-acting connecting member, one of which is located on said handle support and the other of which is located on mounting end, for pivotally attaching said handle to said handle support to enable the handle to be pivoted relative to the laparoscope and for passing therethrough said light carrier and electrical conductors wherein said light carrier and electrical conductors are enclosed by said handle support, said handle and said first co-acting member and said second co-acting connecting member.

9. A video operating laparoscope comprising:
a laparoscope having a proximal end and an image transferring member for producing an optical image at said proximal end;
a video camera operatively connected to said proximal end for receiving said optical image; and
a handle assembly including
a handle support operatively connected to the proximal end of a laparoscope; and
a handle including a mounting end, and
means operatively connected to said handle support and said mounting end for pivotally attaching said handle to said handle support to enable the handle to be pivoted relative to the laparoscope.

10. The video operating laparoscope of claim 9 wherein said pivotally attaching means further includes means for fixing said handle at one of a number of selected pivoted positions relative to said laparoscope.

11. The video operating laparoscope of claim 10 wherein said pivotally attaching means includes a first co-acting member and second co-acting connecting member for attaching said handle to said handle support while enabling said handle to be pivoted about said handle support.

12. The operating laparoscope of claim 11 wherein said light guide member is a fiber optic bundle.

13. The operating laparoscope of claim 10 wherein said image transferring member is a fiber optic image bundle.

14. The operating laparoscope of claim 10 wherein said image transferring member is a lens relay system.

15. The operating laparoscope of claim 14 further comprising a fiberoptic light guide.

16. The operating laparoscope of claim 10 wherein said image transferring member is a GRIN lens system.

17. An operating laparoscope comprising:
a laparoscope having an elongated central axis which extends from a proximal end to a distal end, said laparoscope having an image transferring member, a light guide member and at least one working channel, each of which extend from said proximal end to said distal end of the laparoscope;
a video camera having a sensor operatively connected to the image transferring member at the proximal end of said laparoscope;
a handle support rigidly operatively coupled to the proximal end of the laparoscope, said handle support having a support axis which extends in a spaced relation from and substantially parallel to the central axis of said laparoscope;
a handle having a mounting end; and
a connecting means located on said handle support for pivotally operatively coupling said mounting end of the handle to the handle support to enable said handle to be pivoted relative to the support axis and the central axis of said laparoscope.

18. The operating laparoscope of claim 17 further comprising an inlet port located at the proximal end of the laparoscope and operatively connected to the at least one working channel, said inlet port and said at least one working channel being sized to pass a working tool to the distal end of the laparoscope.

19. The operating laparoscope of claim 18 wherein said laparoscope has a second channel substantially parallel to said at least one working channel and a inlet port operatively connected to said second channel at the proximal end of the laparoscope.

20. The operating laparoscope of claim 18 wherein said laparoscope has at least a working channel and an accessory channel.

21. The operating laparoscope of claim 20 wherein the accessory channel terminates in a nozzle for directing a fluid flow over the distal end of the laparoscope to remove debris therefrom.

22. The video operating laparoscope of claim 17 further comprising a beam splitter for directing a portion of an optical image along a first path and the remaining portion of the optical range along a second path.

23. The operating laparoscope of claim 22 wherein a CCD sensor is positioned along one of said first and second paths to receive an optical image.

24. The operating laparoscope of claim 17 wherein said connecting means further comprises
   a central hub having an outer surface located on said handle support; and
   a hollowed-out central area having an inner wall located on said mounting end operatively connected to said handle support wherein said central hub is located within said hollowed-out central area and the central hub cooperates with the inner wall of said hollowed-out central area to enable said handle to pivot about said central hub.

25. The operating laparoscope of claim 24 wherein said outer surface includes a circumferential groove formed therein which extends substantially perpendicular to and communicates with the outer surface and a bearing member, said mounting end further including
   a resilient engaging member positioned within said mounting end and extending towards the outer surface, said resilient engaging member being adapted to cooperate with and slideably engage said circumferential groove to movably attach said handle to said handle support.

26. The operating laparoscope of claim 24 wherein said central hub has an end plate located substantially perpendicular to the outer surface and wherein the end plate has a plurality of locking slots formed and said mounting end has a resilient locking member for cooperating with said plurality of locking slots to fix said handle at a selected angular position relative to the central axis of said laparoscope.

27. The operating laparoscope of claim 24 wherein said handle support is a "L" shaped elongated thin walled tubular member having hollowed out central area which communicates with an elongated slot located adjacent said and plate.

28. The operative laparoscope of claim 24 wherein said handle support includes an end plate which is substantially perpendicular to the outer surface and wherein said end plate includes a connecting member rigidly connected thereon.

29. The operating laparoscope of claim 28 further comprising a fastening member operatively connected to said connecting member for movably attaching said handle to said handle support while enabling said handle to be pivoted around said connecting member.

30. The operating laparoscope of claim 29 wherein said connecting member is a threaded member and wherein said fastening member is a co-acting threaded member for attaching said handle to said handle support.

31. The operating laparoscope of claim 29 wherein said connecting member is in the form of a raised collar having a groove formed therearound and wherein said fastening member is a snap ring adapted to cooperate with said groove for movably attaching said handle to said handle support.

32. A video operating laparoscope comprising:
   an elongated sheath having a proximal end, a distal end and a hollowed-out central area extending therethrough;
   an image transferring member located in said hollowed-out central area of the elongated sheath, said image transferring member extending from the distal end to the proximal end of the elongated sheath and being adapted to transmit to the proximal end of the elongated sheath an image from an operating area adjacent the distal end of the elongated sheath;
   a light guide member which is located in said hollowed-out central area of the elongated sheath, said light guide member extending from the distal end to the proximal end of the elongated sheath and being adapted to transmit light energy from the proximal end of the elongated sheath to the distal end of the elongated sheath to illuminate the operating area adjacent the distal end of the elongated sheath;
   an operating channel located in said hollowed-out central area of the elongated sheath, said operating channel extending from the distal end to the proximal end of the elongated sheath and being adapted to pass a working tool to an operative area adjacent the distal end of the elongated sheath;
   a housing member located at the proximal end of the elongated sheath, said housing member enclosing said image transferring member, said light guide member and said operating channel, said housing member further enclosing a video sensor operatively coupled to the image transferring member, an entry port which communicates with said operating channel member having a passageway which enables an electrical conductor to be operatively connected to said video sensor and the light conducting member to be operatively connected to a light guide member located at the proximal end of the elongated sheath;
   a handle support assembly having a handle support member operatively connected to the proximal end of the elongated sheath, said handle operative assembly including a handle pivotally operatively connected to said handle support member for enabling pivoting of said handle around said elongated sheath, said handle support member having a passageway for an electrical conductor which extends from said handle through said housing support member to said video sensor for passing video signals and a light guide which extends from said handle through said housing support member to said light conducting member for passing light energy to said light conducting member.

33. The video operative laparoscope of claim 32 wherein said handle support member is in the form of an elongated "L" shaped thin walled cylindrical shaped housing having an outer surface and an end plate located substantially perpendicular to said outer surface, said outer surface having a recessed opening formed therein and said end plate having a plurality of recessed areas formed therein.

34. A system for performing a laparoscopic procedure comprising:
   a laparoscope comprising a rigid elongated sheath tube having an elongated axis, a distal section and a proximal section which terminates in a proximal end, said distal section having a means for defining a distal tip including fluid tight distal lens, said distal lens having an exterior surface located at said distal tip;
   a pivotal handle assembly for an endoscope having a proximal end comprising a handle support operatively connected to the proximal end of an endoscope;

a handle including a mounting end;

means operatively coupled to said handle support and said mounting end for pivotally attaching said handle to said handle support;

means for defining within said laparoscope an image transferring means which extends from the distal tip to the proximal end of the rigid elongated sheath tube;

means for defining within said laparoscope a fiber optic light guide means which extends from the distal tip to the proximal end of the rigid elongated sheath tube;

means for defining within said laparoscope a video sensor;

a video signal processing means operatively coupled to the video sensor for processing a video image of the laparoscopy procedure; and a light source operatively connected to the fiber optic light guide means at the proximal end of the laparoscope.

35. The system of claim 34 wherein said laparoscope further includes means located within said rigid elongated sheath tube for defining at said distal tip a nozzle for directing a fluid flow across the exterior surface of said distal lens to remove therefrom optical image impeding agents;

means defining a first channel which extends axially from the proximal end of the rigid elongated sheath tube to the distal tip thereof, said first channel being operatively coupled to said means defining said nozzle, said first channel including means for defining the proximal end an opening which is adapted to be operatively connected to a source of pressurized fluid;

means for defining a second channel which extends axially from the proximal end of the rigid elongated sheath tube to the distal tip thereof;

means for defining an orifice for directing a stream of fluid along a path which is substantially in alignment with the direction of view of said image transferring means; and means including a source of fluid under pressure operatively connected to the proximal end of the laparoscope for selectively applying fluid under pressure to at least one of said first channel to direct a fluid flow across the exterior surface of the transparent member and said second channel to produce an irrigating fluid along a path substantially parallel to the direction of view of the laparoscope.

36. The system of claim 34 further comprising a source of insufflation gas and a regulator for controlling the flow rate and pressure of the insufflation gas within a cavity in a patient's body operatively connected to the source of insufflation gas.

* * * * *